United States Patent [19]

Ohtsuka

[11] 4,017,533
[45] Apr. 12, 1977

[54] DIAMINOMALEONITRILE DERIVATIVES AND PROCESSES FOR PREPARING THE SAME

[75] Inventor: Yozo Ohtsuka, Sagamihara, Japan

[73] Assignee: Sagami Chemical Research Center, Tokyo, Japan

[22] Filed: Dec. 29, 1975

[21] Appl. No.: 645,179

[30] Foreign Application Priority Data

Dec. 27, 1974 Japan ............................ 49-148714
Dec. 27, 1974 Japan ............................ 49-148715

[52] U.S. Cl. ..................... 260/465 E; 260/250 BN; 260/465 D; 260/465.4; 260/465.5 R; 424/250
[51] Int. Cl.² ............. C07C 120/00; C07C 121/45; C07C 121/78; C07C 121/84
[58] Field of Search ................. 260/465.5 R, 465 E

[56] References Cited

UNITED STATES PATENTS

| | | | |
|---|---|---|---|
| 3,778,446 | 12/1973 | Weigert | 260/465.5 R X |
| 3,806,517 | 4/1974 | Begland | 260/465.5 R X |
| 3,883,532 | 5/1975 | Begland | 260/465.5 R X |
| 3,914,279 | 10/1975 | Begland | 260/465.5 R |

OTHER PUBLICATIONS

House, Modern Synthetic Reactions, 1972, pp. 73–75.

*Primary Examiner*—Joseph Paul Brust
*Attorney, Agent, or Firm*—Sughrue, Rothwell, Mion, Zinn & Macpeak

[57] ABSTRACT pg,1 N-α-Cyanoalkyl compounds of diaminomaleonitrile represented by the formula (I)

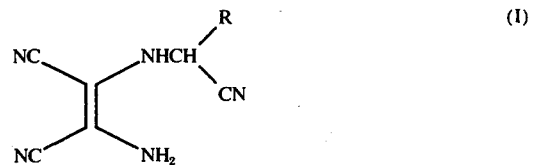

wherein R represents a straight or branched chain alkyl group having 1 to 4 carbon atoms or a phenyl group useful for producing dihydropyrazine compounds; iminonitrile compounds of diaminomaleonitrile useful as antimicrobial agents and intermediates, represented by the formula (II)

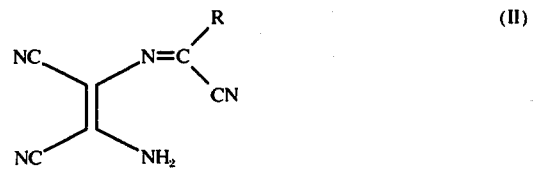

wherein R is as defined above; and processes for preparing the same.

5 Claims, No Drawings

DIAMINOMALEONITRILE DERIVATIVES AND PROCESSES FOR PREPARING THE SAME

BACKGROUND OF THE INVENTION

1. Field of the Invention

This invention relates to novel derivatives of diaminomaleonitrile (DAMN). More particularly, this invention relates to N-α-cyanoalkyl compounds of diaminomaleonitrile represented by the formula (I)

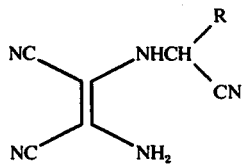  (I)

wherein R represents a straight or branched chain alkyl group having 1 to 4 carbon atoms or a phenyl group; to iminonitrile compounds of diaminomaleonitrile represented by the formula (II)

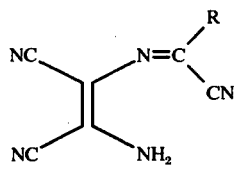  (II)

wherein R is as defined above; and to processes for preparing the compounds of the formulae (I) and (II) above.

2. Description of the Prior Art

Hitherto, it was well known that a Schiff base formed between DAMN and an aldehyde represented by the formula (A)

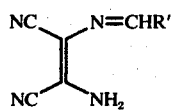  (A)

wherein R' represents an alkyl group or an aryl group can be reduced with sodium borohydride to form the corresponding N-alkyl- or N-aryl compounds represented by the formula (B)

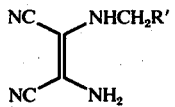  (B)

wherein R' is as defined above, as disclosed in R. N. Begland et al., *J. Org. Chem.*, 39, 2341 (1974). However, the reaction of diaminomaleonitrile with acyl cyanides which belong to a chemical class different from aldehydes has not been reported previously. The different feature of the reaction between the reactions with aldehydes and with acyl cyanides is apparent from the fact that the Schiff base of the formula (A) has not been obtained from lower alkyl aldehydes but from aromatic aldehydes while the iminonitrile compounds of the formula (II) can be obtained readily from lower alkyl acyl cyanides as well as aromatic acyl cyanides.

Moreover, the products of the present invention having the formulae (I) and (II) can be cyclized readily into pyrazine derivatives, but the cyclization of the compounds of the formula (A) gives imidazole derivatives and, in fact, no report has been found with respect to self-condensation of the compounds of the formula (B) to form cyclic compounds.

SUMMARY OF THE INVENTION

A primary object of this invention is to provide novel iminonitrile compounds derived from diaminomaleonitrile represented by the formula (II) which are useful as intermediates for producing a wide variety of cyclic compounds and which per se have antimicrobial activities.

Another object of this invention is to provide novel N-α-cyanoalkyl compounds derived from diaminomaleonitrile represented by the formula (I) which are useful for producing a wide variety of cyclic compounds.

A further object of this invention is to provide processes for preparing the iminonitrile compounds of the formula (II) and N-α-cyanoalkyl compounds of the formula (I) from diaminomaleonitrile.

DETAILED DESCRIPTION OF THE INVENTION

As a result of extensive studies, it was found that the iminonitrile compounds represented by the formula (II) are useful as intermediates for producing a wide variety of compounds which are useful as pharmaceuticals, for example, antimicrobial agents, and novel type amino acids.

Further, it was found that the iminonitrile compounds represented by the formula (II) above can be prepared by reacting diaminomaleonitrile with an acyl cyanide represented by the formula (III)

RCOCN  (III)

wherein R is as defined above, under acidic conditions.

The iminonitrile compounds of the formula (II) can be used for producing pyrazine compounds which are expected to have useful pharmaceutical activities. For example, the iminonitrile compounds can easily be cyclized by heating and then, optionally, hydrolyzed to form pyrazine compounds represented by the formula (IV)

  (IV)

wherein R is as defined above, and X is O or NH. These compounds of the formula (IV) can be converted into xanthopterin type compounds. Also, the pyrazine compounds of the formula (IV) above have a chemical structure closely related to aspergillic acid type compounds as reported in, for example, Mitsuo Masaki, Journal of Synthetic Organic Chemistry, Japan, Vol. 25, 750 (1961) and have a utility as antimicrobial agents and intermediates for the synthesis of such antimicrobial agents. For example, the above pyrazine compounds can be converted into the compounds having a partial structure:

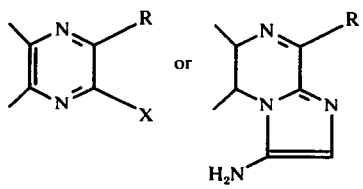

wherein R and X are as defined above, using a well-known procedure as described in Japanese Patent Application Laid Open Public Inspection No. 29379/1972. These partical structures are sometimes found in the known anti-bronchospasm agents and, therefore, the above pyrazine compounds are expected to be useful in producing antitussive or antiasthmatic agents.

In addition, it was well known that dicyanopyrazine compounds can be converted into phthalocyanine compounds as reported in R. P. Linstead, E. G. Noble and J. M. Wright, *J. Chem. Soc.*, 911 (1937) and H. W. Rothkopf, D. Wohrle, R. Muller and G. Kossmehl, *Chem. Ber.*, 108, 875 (1975) and, therefore, the above pyrazine compounds can be used for producing such phthalocyanine dyes or pigments.

In addition to the above utilities, the iminonitrile compounds of the formula (II) per se exhibit an antimicrobial acitivity against rice blast and sheath blight infections as described hereinafter in detail in Reference Example 4.

It was also found that the iminonitrile compounds of the formula (II) can be easily reduced with sodium borohydrodie to form N-$\alpha$-cyanoalkyl compounds represented by the formula (I) above. In contrast to the prior art diaminomaleonitrile derivatives, the N-$\alpha$-cyanoalkyl compounds of the formula (I) can easily be self-cyclized as described hereinafter in detail in Reference Examples 1 to 3 by merely heating the N-$\alpha$-cyanoalkyl compounds in a solvent such as ethanol to form the corresponding dihydropyrazine compounds represented by the formula (VI)

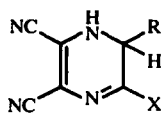

wherein R is as defined above and X represents OH or $NH_2$.

Thus, the present invention includes a process for preparing N-$\alpha$-cyanoalkyl compounds of the formula (I) from diaminomaleonitrile through the intermediate, iminonitrile compounds of the formula (II) above, as well as the process for preparing the iminonitrile compounds of the formula (II) from diaminomaleonitrile.

Still further, suitably protected aminonitrile compounds of the formula (I) can be hydrolyzed to form the derivatives essentially having the formula (V)

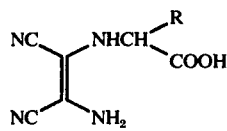

wherein R is as defined above. These novel type amino acids also can further be converted into various amino acids.

As previously described, the process of this invention comprises reacting diaminomaleonitrile with an acyl cyanide of the formula (III) to produce the corresponding iminonitrile compound of diaminomaleonitrile of the formula (II) and, optionally, reducing the resulting iminonitrile compound with sodium borohydride to obtain the corresponding cyanoalkyl compound of the formula (I).

The first step of the process of this invention comprises reacting diaminomaleonitrile with an acyl cyanide of the formula (III)

$$RCOCN \qquad (III)$$

wherein R is as defined above, under acidic conditions.

The acidic conditions required in the first step can easily be attained by using a small amount, generally in a so-called catalytic amount of an inorganic acid such as hydrohalic acid, e.g., hydrochloric acid, hydrobromic acid and the like, sulfuric acid, phosphoric acid and the like, or an organic acid such as sulfonic acid, e.g., p-toluene-sulfonic acid, carboxylic acids, e.g., formic acid, acetic acid and the like. Alternatively, a compound which is capable of providing an acid in situ upon addition to a reaction system of diaminomaleonitrile and an acyl cyanide, for example, phosphorus pentoxide, acid anhydrides such as acetic anhydride can also be used.

In carrying out the reaction, solvents are not necessarily required, but in order to ensure a smooth reaction, it is preferred to use an inert organic solvent which does not adversely affect the reaction between diaminomaleonitrile and the acyl cyanide of the formula (III) as well as the desired iminonitrile compound represented by the formula (II). Suitable examples of the solvents which can be used in the reaction are alcohols having 1 to 3 carbon atoms such as methanol, ethanol, isopropanol and the like, ethers such as diethyl ether, tetrahydrofuran and the like, esters such as ethyl acetate and the like, hydrocarbons such as benzene and the like, and mixtures thereof. Preferred examples of solvents are methanol or ethanol.

The reaction can be carried out at an equimolar proportion of the reactants, diaminomaleonitrile and the acyl cyanide of the formula (II), but the acyl cyanide is preferably used in a slightly excess amount, e.g., about 1.3 moles per mole of diaminomaleonitrile. The reaction temperature can range from about 0° to about 50° C, but is preferably room temperature (about 20°–30° C). This reaction is generally exothermic in nature and can preferably be conducted while cooling the reaction mixture, for example, by cooling a reaction vessel with water or ice-water. Also, the reaction mixture is preferably stirred during the reaction to ensure a smooth and uniform reaction.

The reaction time varies depending upon the reaction temperature used and, in some instances, the reaction occurs almost instantaneously. However, the reaction time generally ranges from about 5 minutes to about 30 minutes at room temperature whereby the desired iminonitrile intermediate (II) can be obtained in satisfactory yield.

The reaction product is generally recovered from the reaction mixture by crystallization using a conventional procedure and can be purified in a well-known manner, for example, recrystallization. However, the product generally has a purity sufficient to use the product without purification in subsequent steps, e.g., a reduction reaction with sodium borohydride, when the reaction is conducted under optimum conditions.

The acyl cyanide represented by the formula (III) above are generally commercially available as industrial materials or can easily be produced by reacting copper cyanide with an organic acid halide having an acyl group (RCO) corresponding to the acyl group in the acyl cyanide of the formula (III), according to a conventional procedure, for example, the process described in W. Tschelinzeff and W. Schmidt., Chem. Ber., 62, 2210 (1929).

The second step of the process of this invention comprises reducing the above obtained iminonitrile compound of the formula (II) with sodium borohydride as a reducing agent.

In carrying out the reduction, at least about 2 moles, preferably 2 to 4 moles, of sodium borohydride is used per mole of the iminonitrile compound of the formula (II).

The reduction is generally conducted in an organic polar solvent at preferably room temperature (about 20° to 30° C). This reaction is also exothermic in nature and cooling as set forth in the first step can preferably be used.

Examples of the solvent which can be used in the reduction of the iminonitrile compound of the formula (II) are alcohols having 1 to 3 carbon atoms such as methanol, ethanol and the like, tetrahydrofuran, dioxane or a mixture thereof. Such solvents can preferably be used in such a proportion that the reduction system contains the minonitrile compound at a concentration of about 1 to about 20% by weight. Of course, lower or higher concentrations can be used, if desired.

In the reduction, sodium borohydride is preferably added in small portions to a solution of the iminonitrile compound of the formula (II) dissolved in a solvent as described above in order to avoid vigorous exothermic reactions between the iminonitrile compound and sodium borohydride. The reduction is generally completed upon addition of sodium borohydride.

The reduction product having the formula (I) above can be isolated from the reduction system using a well-known technique, for example, by pouring the reaction mixture into ice-water to crystallize the product, followed by filtration. The product thus obtained can be purified further by recrystallization, if desired.

The present invention is further illustrated by the following Examples in greater detail, but they are given for illustrative purposes only and not to be construed as limiting the present invention. Unless otherwise indicated, all percents, ratios, parts and the like are by weight.

EXAMPLE 1

To a mixture of 30 g of diaminomaleonitrile and 30.5 g of isobutyronitrile were added a catalytic amount of phosphorus pentoxide and then several drops of absolute methanol whereby an exothermic reaction occurred. The reaction mixture was stirred while cooling the reaction vessel in cooled water for about 5 minutes to complete the reaction. The resulting reaction mixture was placed on a glass filter and the liquid phase was removed by suction filtration, and the filter cake remaining on the filter was washed with a small amount of cold methanol and dried under reduced pressure to obtain 38.65 g (75.8% yield) of crystals. The crystals thus obtained showed an infrared absorption spectrum identical to that of an authentic sample of α-cyanoisobutenylidenediaminomaleonitrile and found to have a purity sufficient to be used in a subsequent reaction. For analysis, a sample of the above crystals was repeatedly recrystallized from methano containing a small amount of water to obtain α-cyanoisobutenylidenediaminomaleonitrile having a melting point of 151.5°–153.0° C.

Elementary Analysis: Calcd. for $C_9H_9N_5$: C, 57.74; H, 4.85; N, 37.71(%). Found: C, 57.48; H, 4.86; N, 37.26(%).

EXAMPLE 2

3.0 g of phosphorus pentoxide was dissolved in 30 ml of substantially absolute methanol, and to the resulting solution were added 5.41 g of diaminomaleonitrile and 6.64 g of benzoyl cyanide. After 5 to 7 minutes, the resulting reaction mixture turned into an orange-colored slurry. The slurry was filtered using a glass filter (No. 4) under pressurized condition by introducing nitrogen gas to obtain 5.55 g (50.5% yield) of a product as a yellow solid. A sample of the product thus obtained was recrystallized from ethyl acetate to obtain a yellow crystalline powder having a melting point of 185°–186° C. The infrared and NMR spectra of the product showed characteristic absorptions due to α-cyanobenzylidenediaminomaleonitrile structure, and the mass spectrum showed $M^+$ 221.

Elementary Analysis: Calcd. for $C_{12}H_7N_5$: C, 65.15; H, 3.17; N, 31.66(%). Found: C, 65.15; H, 3.15; N, 31.54(%).

EXAMPLE 3

A mixture of 16 g of diaminomaleonitrile and 12.6 g of acetyl cyanide was stirred with a glass rod whereby an exothermic reaction occurred and the resulting reaction mixture turned into a yellow-colored mixture. After allowing the mixture to stand for 10 minutes, the mixture was washed with small amount of cooled methanol and dried under reduced pressure to obtain 22.65 g (95.9% yield) of crude crystals of α-cynoethylidenediaminomaleonitrile which was found to have a purity sufficient to be used in subsequent reactions. For analysis, a sample of the above crystals was then repeatedly recrystallized from a mixture of methanol and water (3:2 by volume) to obtain α-cyanoethylidenediaminomaleonitrile having a melting point of 220°–221° C as milky white fine crystals.

Elementary Analysis: Calcd. for $C_7H_5N_5$: C, 52.83; H, 3.17; N, 44.00(%). Found: C, 52.89; H, 2.97; N, 43.99(%).

EXAMPLE 4

A. 10.8 g of diaminomaleonitrile and 10.0 g of acetyl cyanide were added successively to a solution of 1.9 g of p-toluenesulfonic acid in 100 ml of dry diethyl ether. The resulting yellow powder was collected by filtration and dried. The crude product thus obtained was dissolved in 600 ml of acetone and any inseluble insoluble solids were removed by filtration. 900 ml of water was added to the filtrate to obtain α-cyanoethylidenediaminomaleonitrile in 41% yield.

B. To a mixture of 22.1 g of acetyl cyanide and 16.3 g of diaminomaleonitrile were added dropwise a solution of 0.5 g of phosphorus pentoxide in 3 ml of methanol. The crude product thus obtained was recrystallized from aqueous methanol to obtain 6.3 g (26% yield) of α-cyanoethylidenediaminomaleonitrile.

EXAMPLE 5

4.0 g of a Schiff base, α-cyanoethylidenediaminomaleonitrile, obtained from diaminomaleonitrile and acetyl cyanide as described in Examples 3 and 4 was dissolved in a mixture of 40 ml of methanol and 20 ml of tetrahydrofuran, and 3.8 g of sodium borohydride was added in small portions to the resulting solution over a period of about 15 minutes during which time the reaction vessel was occasionally placed into water to cool the reaction mixture. After completion of the reaction, the reaction mixture was poured into about 500 ml of ice-water and the crystals precipitated were collected by filtration and washed with water to obtain 2.2 g (54.3% yield) of α-cyanoethyldiaminomaleonitrile. For analysis, a sample of the product thus obtained was repeatedly recrystallized from hydrous methanol to obtain α-cyanoethyldiaminomaleonitrile having a melting point of 226°–228° C (with decomposition) as orange-colored needles Elementary Analysis: Calcd. for $C_7H_7N_5$: C, 52.17; H, 4.38; N, 43.45(%). Found: C, 52.19; H, 4.24; N, 43.54(%).

EXAMPLE 6

5.0 g of a Schiff base, α-cyanoisobutenylidenediaminomaleonitrile, obtained from diaminomaleonitrile and isobutyronitrile as described in Example 1 was dissolved in a mixture of 20 ml of methanol and 12.5 ml of tetrahydrofuran, and 3.0 g of sodium borohydride was added in small portions to the resulting solution over a period of about 15 minutes. After completion of the addition, the reaction mixture was poured into 500 ml of ice-water and the pale yellow fine crystals precipitated were collected by filtration to obtain 3.35 g (66.3% yield) of α-cyanoisobutyldiaminomaleonitrile. A sample of the product thus obtained was repeatedly recrystallized from a methanol-water mixture (3:4 by volume) to obtain a product having a melting point of 231°–235° C (with decomposition) as a pale brown crystalline powder.

Elementary Analysis: Calcd. for $C_9H_{11}N_5$: C, 57.13; H, 5.86; N, 37.01(%). Found: C, 57.13; H, 5.82; N, 36.92(%).

EXAMPLE 7

3.85 g of a Schiff base, α-cyanobenzylidenediaminomaleonitrile, obtained from diaminomaleonitrile and benzoyl cyanide as described in Example 2 was dissolved in a mixture of 70 ml of methanol and 100 ml of tetrahydrofuran, and 2.2 g of sodium borohydride was added in small portions to the resulting solution over a period of about 15 minutes. After completion of the addition, the reaction mixture was poured into about 500 ml of ice-water. The crystals precipitated was collected by filtration, washed with water and dried to obtain 2.3 g (59.2% yield) of α-cyanobenzyldiaminomaleonitrile. A sample of the product thus obtained repeatedly recrystallized from a methanol-water mixture (2:3 by volume) to obtain α-cyanobenzyldiaminomaleonitrile having a melting point of 205°–206° C (with decomposition) as colorless needles.

Elementary Analysis: Calcd. for $C_{12}H_9N_5$: C, 64.56; H, 4.06; N, 31.37(%). Found: C, 64.49; H, 3.89; N, 31.39(%).

REFERENCE EXAMPLE 1

1.5 g of the α-cyanobenzylidenediaminomaleonitrile obtained as described in Example 2 was heated under refluxing in 80 ml of ethanol. Upon containing the heating, the initial heterogeneous yellow solution turned into a uniform solution and then turned into a red-brown solution. Thereafter, the ethanol was distilled off under reduced pressure, and 1.5 g (almost quantative yield) of crystals was recovered from the resulting residue. The infrared absorption spectrum of the product thus obtained was found to be quite consistent with an authentic sample of 2-amino-3-phenyl-5,6-dicyanopyrazine. For analysis, a sample of the product was repeatedly recrystallized from a methanol-water mixture to obtain 2-amino-3-phenyl-5,6-dicyanopyrazine having a melting point of 167°–168° C.

Elementary Analysis: Calcd. for $C_{12}H_7N_5$: C, 65.15; H, 3.19; N, 31.66 (%). Found: C, 65.17; H, 3.18; N, 31.72(%).

REFERENCE EXAMPLE 2

A mixture of 0.78 g of α-cyanobenzyldiaminomaleonitrile obtained as described in Example 6, 0.5 of phosphorus pentoxide and 30 ml of ethanol were heated under refluxing for 19 hours, and then the ethanol was distilled off under reduced pressure. Water was added to the resulting residue, and the crystals precipitated were collected by filtration and dried to obtain 0.5 g (64% yield) of 2-phenyl-3-hydroxy-5,6-dicyano-1,2-dihydropyrazine. For analysis, a sample of the product thus obtained was repeatedly recrystallized from a methanol-water mixture (1:1 by volume) to obtain 2-phenyl-3-hydroxy-5,6-dicyano-1,2-dihydropyrazine having a melting point of 222°–224° C as orange-yellow colored crystals.

Elementary Analysis: Calcd. for $C_{12}H_{18}N_4O$: C, 64.28; H, 3.59; N, 24.98(%). Found: C, 64.12; H, 3.60; N, 24.98(%).

When the above reaction was conducted in the presence of benzaldehyde, the same product as above was obtained in a yield of 94.6%.

REFERENCE EXAMPLE 3

A mixture of 1.0 g of α-cyanoethyldiaminomaleonitrile obtained as described in Example 4 and 0.3 g of phosphorus pentoxide was heated under refluxing for 19 hours in 30 ml of ethanol. Thereafter, the solvent was distilled off, and the resulting residue was treated with ice-water to obtain brown-colored fine crystals. The crystals thus obtained were recrystallized from a mixture of tetrahydrofuran, methanol and water (2:2:1 by volume) to obtain 0.72 g (72% yield) of 5,6-dicyano-2-methyl-1,2,3,4-tetrahydropyrazin-3-one having a melting point of 243°–245° C as a white powder.

Elementary Analysis: Calcd. for $C_7H_6N_4O$: C, 51.85; H, 3.73; N, 34.55(%). Found: C, 51.63; H, 3.78; N, 34.80(%).

REFERENCE EXAMPLE 4

The antimicrobial activity of α-cyanoethylidenediaminomaleonitrile (Compound A) obtained in Example 3 and α-cyanoisobutenylidenediaminomaleonitrile (Compound B) obtained in Example 1 was tested against the rice blast and sheath blight infections. In this test, each of the test compounds was sprayed at a concentration of 500 ppm to the 4-5 leaf-stage rice plant in pots. The rice plant was then inoculated with the organism of the rice blast or sheath blight infection and incubated at a temperature of 23° to 28° C at a high humidity for one week. The degree of infection was then observed and the inhibitory effect of the test compounds was evaluated in 5 grades, i.e., no infection (P=0) to complete infection (P=4). The test results demonstrated that Compound A is effective against both the rice blast (P=1.5) and the sheath blight (P=1) and Compound B is effective against sheath blight (P=1.5).

While the invention has been described in detail with reference to specific embodiments thereof, it will be apparent to one skilled in the art that various modifications and changes can be made therein without departing from the spirit thereof.

What is claimed is:

1. N-α-Cyanoalkyl compounds of diaminomaleonitrile represented by the formula (I)

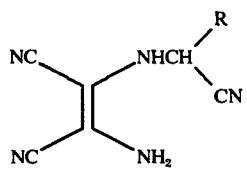

wherein R represents a straight or branched chain alkyl group having 1 to 4 carbon atoms or a phenyl group.

2. Iminonitrile compounds of diaminomaleonitrile represented by the formula (II)

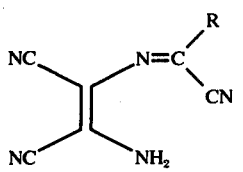

wherein R represents a straight or branched chain alkyl group having 1 to 4 carbon atoms or a phenyl group.

3. A process for preparing an iminonitrile compound of diaminomaleonitrile represented by the formula (II)

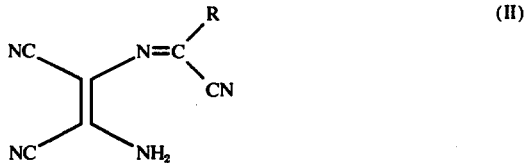

wherein R represents a straight or branched chain alkyl group having 1 to 4 carbon atoms or a phenyl group, which comprises reacting diaminomaleonitrile with an acyl cyanide represented by the formula (III)

wherein R is as defined above, under acidic conditions at a temperature of about 0° to about 50° C at a molar ratio of about 1 to about 1.3 moles of said acyl cyanide per mole of diaminomaleonitrile.

4. A process for preparing an N-α-cyanoalkyl compound of diaminomaleonitrile represented by the formula (I)

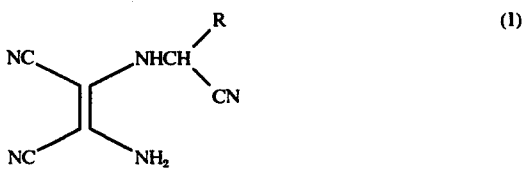

wherein R represents a straight or branched chain alkyl group having 1 to 4 carbon atoms or a phenyl group, which comprises reacting diaminomaleonitrile with an acyl cyanide represented by the formula (III)

wherein R is as defined above, under acidic conditions at a temperature of about 0° to about 50° C at a molar ratio of about 1 to 1.3 moles of said acyl cyanide per mole of diaminomaleonitrile to produce the corresponding iminonitrile compound represented by the formula (II)

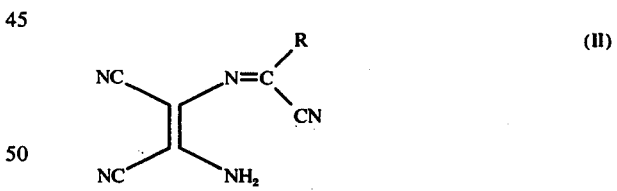

wherein R is as defined above, and reducing the resulting iminonitrile compound with sodium borohydride at a molar ratio of about 2 to 4 moles of sodium borohydride per mole of said iminonitrile compound in an organic polar solvent.

5. The process according to claim 4, wherein said organic polar solvent is methanol, ethanol, tetrahydrofuran, dioxane or a mixture thereof.

* * * * *